US012611183B2

(12) United States Patent
Ouyang et al.

(10) Patent No.: US 12,611,183 B2
(45) Date of Patent: Apr. 28, 2026

(54) CONTRAST ENHANCED IMAGING METHOD AND ULTRASONIC IMAGING SYSTEM

(71) Applicant: SHENZHEN MINDRAY BIO-MEDICAL ELECTRONICS CO., LTD., Guangdong (CN)

(72) Inventors: Yali Ouyang, Shenzhen (CN); Maodong Sang, Shenzhen (CN); Donghai Qin, Shenzhen (CN); Bo Yang, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 24 days.

(21) Appl. No.: 18/373,272

(22) Filed: Sep. 26, 2023

(65) Prior Publication Data

US 2024/0099700 A1     Mar. 28, 2024

(30) Foreign Application Priority Data

Sep. 28, 2022    (CN) .......................... 202211194333.3

(51) Int. Cl.
*A61B 8/00*          (2006.01)
(52) U.S. Cl.
CPC ............ *A61B 8/5207* (2013.01); *A61B 8/481* (2013.01)
(58) Field of Classification Search
CPC .......................... A61B 8/481; G01S 7/52039
See application file for complete search history.

(56) References Cited

U.S. PATENT DOCUMENTS

| | | | | |
|---|---|---|---|---|
| 2011/0077516 A1* | 3/2011 | Abe | ..................... | A61B 8/0883 |
| | | | | 600/443 |
| 2011/0128440 A1* | 6/2011 | Koike | ....................... | G06T 1/00 |
| | | | | 348/E7.003 |
| 2020/0281571 A1* | 9/2020 | Luo | ........................... | A61B 8/54 |
| 2023/0084230 A1* | 3/2023 | Choi | ...................... | A61B 8/461 |
| | | | | 345/428 |

* cited by examiner

*Primary Examiner* — Nyrobi Celestine
(74) *Attorney, Agent, or Firm* — Sheppard Mullin Richter & Hampton LLP

(57) ABSTRACT

A contrast enhanced imaging method and system, under a first mode, include: transmitting ultrasonic waves at a first frame rate to a tissue containing micro-bubbles and receiving echo signals thereof to generate a first contrast enhanced image; transmitting ultrasonic waves at a second frame rate greater than the first frame rate and receiving echo signals thereof to generate a second contrast enhanced image; and generating a super-resolution image; and may, under a second mode, include: transmitting ultrasonic waves at a third frame rate greater than the first frame rate to the target tissue containing the contrast micro-bubbles and receiving echo signals thereof to generate a third contrast enhanced image; freezing the third contrast enhanced image; and generating a super-resolution image based on the echo signals of the third ultrasonic waves for a period of time before freezing. With the present disclosure, users can easily collect the data for super-resolution imaging.

21 Claims, 6 Drawing Sheets

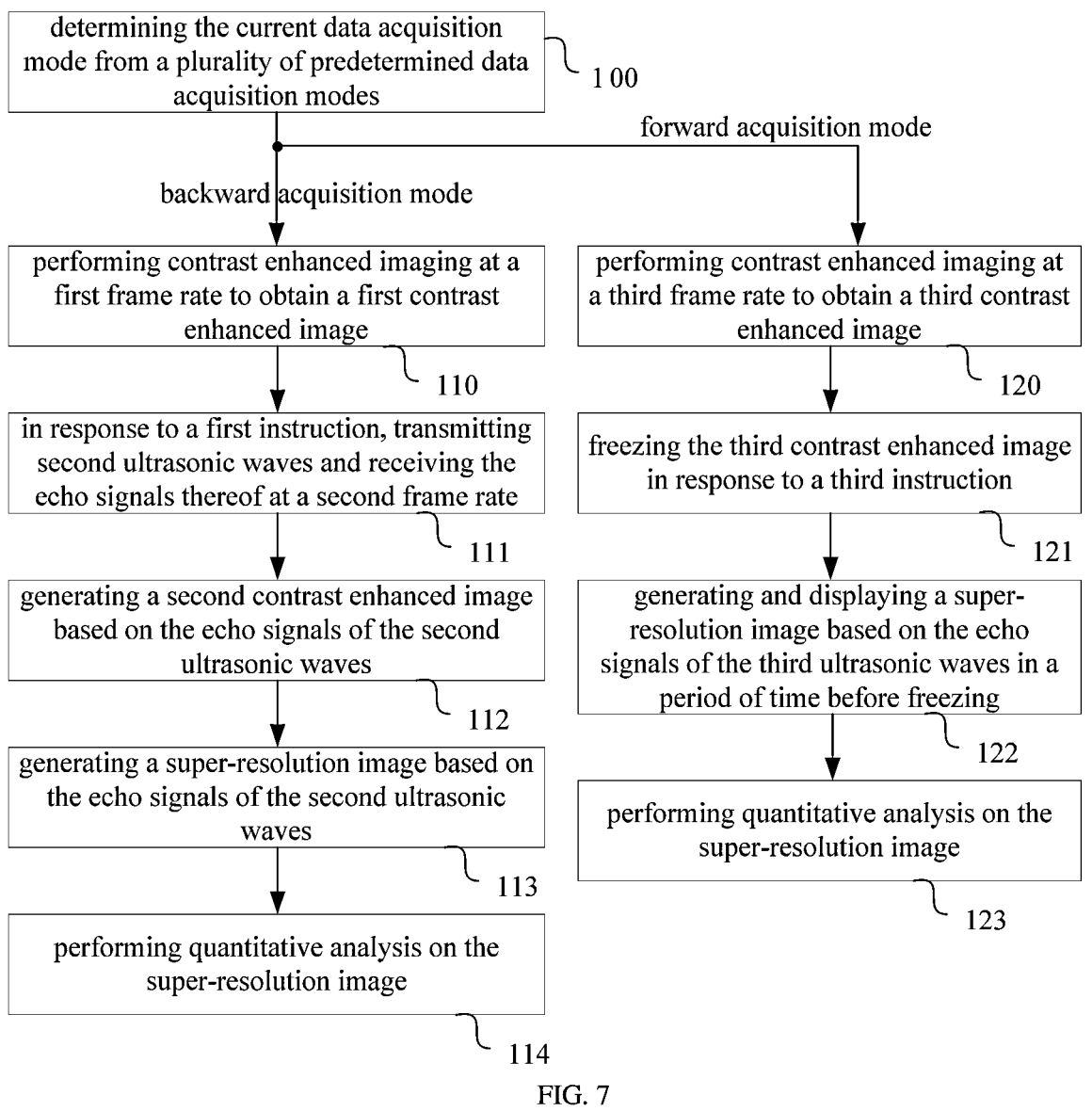

determining the current data acquisition mode from a plurality of predetermined data acquisition modes — 100 forward acquisition mode backward acquisition mode performing contrast enhanced imaging at a first frame rate to obtain a first contrast enhanced image — 110 performing contrast enhanced imaging at a third frame rate to obtain a third contrast enhanced image — 120 in response to a first instruction, transmitting second ultrasonic waves and receiving the echo signals thereof at a second frame rate — 111 freezing the third contrast enhanced image in response to a third instruction — 121 generating a second contrast enhanced image based on the echo signals of the second ultrasonic waves — 112 generating and displaying a super-resolution image based on the echo signals of the third ultrasonic waves in a period of time before freezing — 122 generating a super-resolution image based on the echo signals of the second ultrasonic waves — 113 performing quantitative analysis on the super-resolution image — 123 performing quantitative analysis on the super-resolution image — 114

FIG. 7

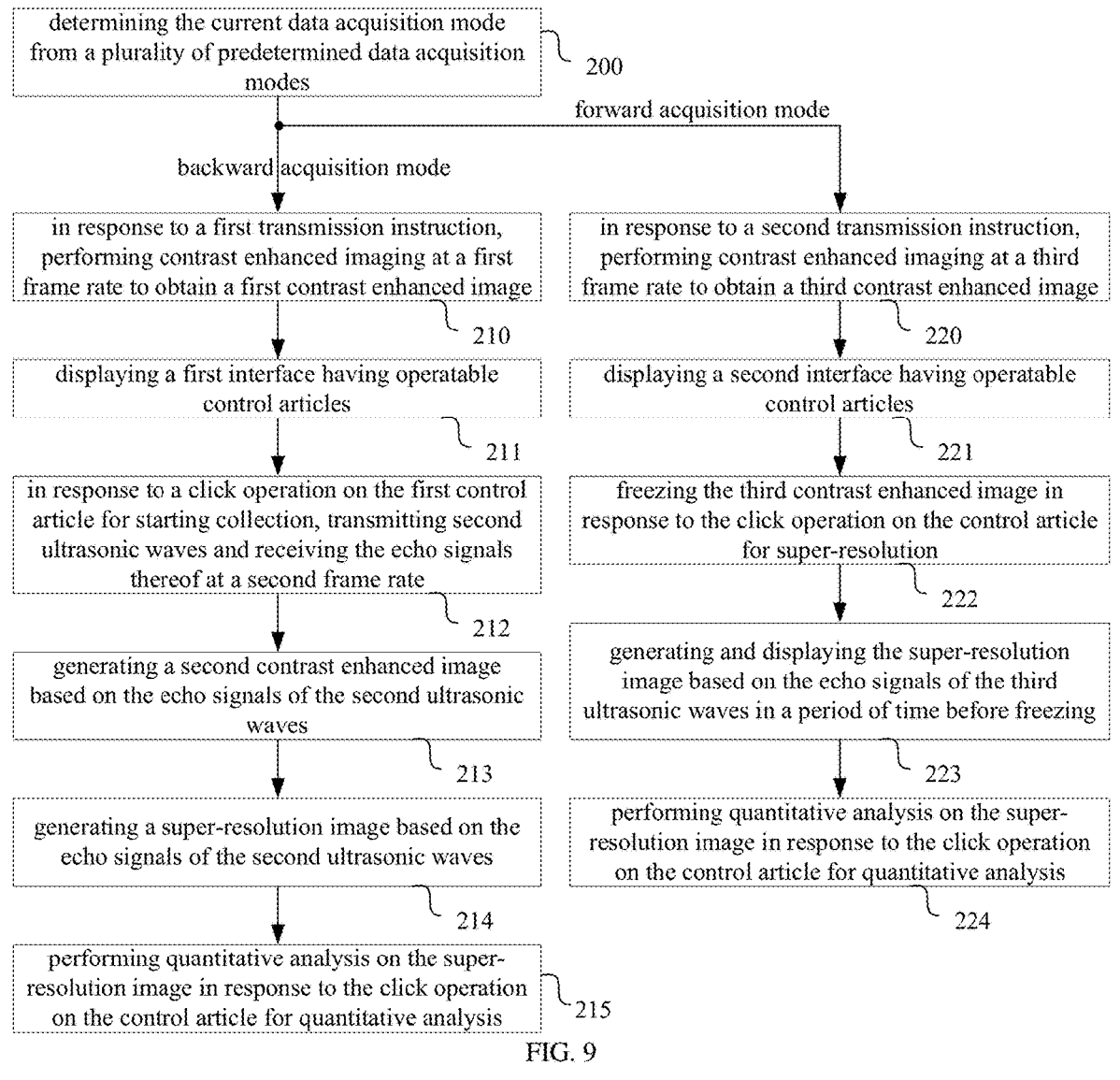

determining the current data acquisition mode from a plurality of predetermined data acquisition modes ⌐ 200 forward acquisition mode backward acquisition mode in response to a first transmission instruction, performing contrast enhanced imaging at a first frame rate to obtain a first contrast enhanced image ⌐ 210 in response to a second transmission instruction, performing contrast enhanced imaging at a third frame rate to obtain a third contrast enhanced image ⌐ 220 displaying a first interface having operatable control articles ⌐ 211 displaying a second interface having operatable control articles ⌐ 221 in response to a click operation on the first control article for starting collection, transmitting second ultrasonic waves and receiving the echo signals thereof at a second frame rate ⌐ 212 freezing the third contrast enhanced image in response to the click operation on the control article for super-resolution ⌐ 222 generating a second contrast enhanced image based on the echo signals of the second ultrasonic waves ⌐ 213 generating and displaying the super-resolution image based on the echo signals of the third ultrasonic waves in a period of time before freezing ⌐ 223 generating a super-resolution image based on the echo signals of the second ultrasonic waves ⌐ 214 performing quantitative analysis on the super-resolution image in response to the click operation on the control article for quantitative analysis ⌐ 224 performing quantitative analysis on the super-resolution image in response to the click operation on the control article for quantitative analysis ⌐ 215

FIG. 9

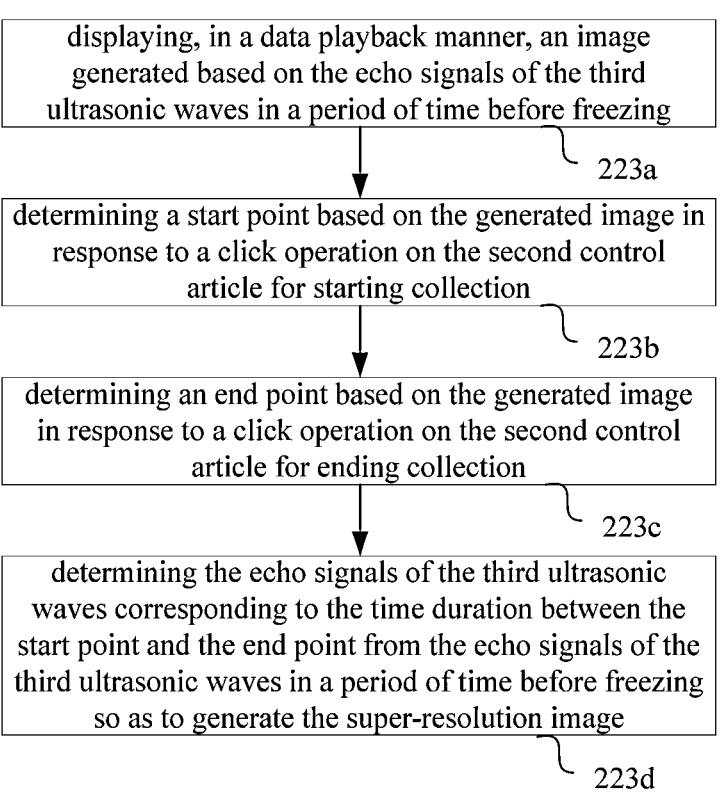

displaying, in a data playback manner, an image generated based on the echo signals of the third ultrasonic waves in a period of time before freezing 223a determining a start point based on the generated image in response to a click operation on the second control article for starting collection 223b determining an end point based on the generated image in response to a click operation on the second control article for ending collection 223c determining the echo signals of the third ultrasonic waves corresponding to the time duration between the start point and the end point from the echo signals of the third ultrasonic waves in a period of time before freezing so as to generate the super-resolution image 223d

CONTRAST ENHANCED IMAGING METHOD AND ULTRASONIC IMAGING SYSTEM

CROSS-REFERENCE TO RELATED APPLICATIONS

This application is based on and claims priority to and benefits of Chinese Patent Application No. 202211194333.3 filed on Sep. 28, 2022. The entire content of the above-referenced application is incorporated herein by reference.

TECHNICAL FIELD

The present disclosure relates to ultrasonic imaging, in particular to contrast enhanced imaging methods and ultrasonic imaging systems.

BACKGROUND OF THE INVENTION

As a new technology that can dynamically observe the blood flow and perfusion of lesions and their tissues in real time, contrast enhanced ultrasound (CEUS) plays an increasingly important role in the diagnosis of malignant diseases such as liver cancer, thyroid cancer and breast cancer, and becomes a necessary examination method for clinical evaluation of blood circulation and perfusion.

Blockage, obstruction and lesion of microcirculation are precursors to many diseases. Observation of microvascular changes is beneficial to the early diagnosis of disease. Capillaries are located in the epidermis and are an important part of blood microcirculation. They have the smallest diameter, about 6~9 μm. The arterioles and venules, with a diameter of 10-100 μm, are located in the dermis and are connected to the arteries and veins in the lower cortex. Microcirculation refers to the blood circulation between arterioles and venules in the vascular network. It is not only the peripheral part of the circulatory system, but also an important part of organs. Usually, the blood flow of microcirculation is adapted to the metabolism levels of human tissues and organs, maintaining normal life activities and metabolism of the human body. When the metabolism and function of tissues and organs are abnormal, microcirculation will undergo a certain extent. Therefore, microcirculation is closely related to the occurrence and development of diseases, and has important physiological, pathological, pharmacological and clinical significance. It is of great value for the early diagnosis and treatment of various diseases.

However, due to the diffraction limit of ultrasound in the far field, the ability of routine CEUS to reveal the details of microvascular structure is limited. Although spatial resolution can be improved by increasing transmission frequency and near-field imaging, it may inevitably lead to a decrease in imaging depth, and most organs are far from the probe depth, making near-field super-resolution methods difficult to apply. Super-resolution CEUS (SR-CEUS), a novel imaging method with ultra-high spatial resolution, can solve the problem of microvascular display and become a powerful tool for observing microvascular flow. It is currently widely used in preclinical research in fields such as tumors, microvascular perfusion of different tissues and organs, and plaque neovascularization.

It is necessary to collect the data for super-resolution imaging, which is very inconvenient at present.

2

SUMMARY OF THE INVENTION

The present disclosure provides contrast enhanced imaging methods and ultrasonic imaging system to solve the problems mentioned above, which are described in detail below.

In accordance with a first aspect, a contrast enhanced imaging method provided in an embodiment may include:

determining a current data acquisition mode from a plurality of predetermined data acquisition modes, the plurality of predetermined data acquisition modes including a backward acquisition mode and a forward acquisition mode;

when the current data acquisition mode is the backward acquisition mode, the method comprising:

transmitting first ultrasonic waves at a first frame rate to a target tissue containing contrast micro-bubbles and receiving echo signals of the first ultrasonic waves to generate and display a first contrast enhanced image in real time based on the echo signals of the first ultrasonic waves;

in response to a first instruction, transmitting second ultrasonic waves at a second frame rate greater than the first frame rate to the target tissue containing contrast micro-bubbles and receiving echo signals of the second ultrasonic waves to generate and display a second contrast enhanced image in real time based on the echo signals of the second ultrasonic waves; and generating and displaying a super-resolution image based on the echo signals of the second ultrasonic waves; and when the current data acquisition mode is the forward acquisition mode, the method comprising:

transmitting third ultrasonic waves at a third frame rate greater than the first frame rate to the target tissue containing contrast micro-bubbles and receiving echo signals of the third ultrasonic waves to generate and display a third contrast enhanced image in real time based on the echo signals of the third ultrasonic waves;

in response to a third instruction, freezing the third contrast enhanced image; and based on the echo signals of the third ultrasonic waves in a period of time before freezing, generating and displaying a super-resolution image.

In an embodiment, generating and displaying a second contrast enhanced image in real time based on the echo signals of the second ultrasonic waves may comprise: extracting partial frames from the echo signals of the second ultrasonic waves, and generating and displaying the second contrast enhanced image based on said partial frames; and generating and displaying a third contrast enhanced image in real time based on the echo signals of the third ultrasonic waves may comprise: extracting partial frames from the echo signals of the third ultrasonic waves, and generating and displaying the third contrast enhanced image based on said partial frames.

In an embodiment, generating and displaying a super-resolution image based on the echo signals of the second ultrasonic waves may comprise: performing super-resolution data processing on the echo signals of the second ultrasonic waves to obtain said super-resolution image; and generating and displaying a super-resolution image based on the echo signals of the third ultrasonic waves in a period of time before freezing may comprise: performing super-resolution data processing on the echo signals of the third ultrasonic waves in a period of time before freezing to obtain said super-resolution image.

In an embodiment, the super-resolution data processing may comprise:

extracting signals for contrast micro-bubbles from echo signals of ultrasonic waves to be processed;

separating the extracted signals for contrast micro-bubbles;

positioning each contrast micro-bubble;

tracking a trajectory of each contrast micro-bubble; and performing image construction based on the positioning and trajectory tracking of each contrast micro-bubble so as to obtain said super-resolution image.

In an embodiment, the contrast enhanced imaging method may further comprise: displaying progress of the super-resolution data processing while performing the super-resolution data processing.

In an embodiment, the contrast enhanced imaging method may further comprise: in response to an instruction for quantitative analysis, performing quantitative analysis on the super resolution image, and displaying an analysis result of the quantitative analysis.

In an embodiment, the contrast enhanced imaging method may further comprise: displaying the second contrast enhanced image and the super-resolution image on a same display interface when the current data acquisition mode is the backward acquisition mode; and/or, displaying the third contrast enhanced image and the super-resolution image on a same display interface when the current data acquisition mode is the forward acquisition mode.

In an embodiment, the contrast enhanced imaging method may further comprise: displaying a duration for the received echo signals of the second ultrasonic waves when the current data acquisition mode is the backward acquisition mode.

In an embodiment, the contrast enhanced imaging method may further comprise: displaying at least one of the following control articles when the current data acquisition mode is the backward acquisition mode:

a control article for starting collection configured to generate the first instruction after being clicked;

a control article for ending collection configured to generate a second instruction after being clicked, the second instruction being used to stop transmitting the second ultrasonic waves and/or stop receiving the echo signals of the second ultrasonic waves;

a control article for timer configured to start timing in response to the first instruction, so as to display the duration; and a control article for quantitative analysis configured to generate the instruction for quantitative analysis after being clicked.

In an embodiment, generating and displaying a super-resolution image based on the echo signals of the third ultrasonic waves in a period of time before freezing may comprise:

displaying, in a data playback manner, an image generated by the echo signals of the third ultrasonic waves in a period of time before freezing;

determining a start point based on the generated image and in response to a fourth instruction;

determining an end point based on the generated image and in response to a fifth instruction; and determining the echo signals of the third ultrasonic waves corresponding to a duration between the start point and the end point from the echo signals of the third ultrasonic waves in a period of time before freezing, so as to generate the super-resolution image.

In an embodiment, the contrast enhanced imaging method may further comprise: starting timing and displaying duration in response to the fourth instruction, and ending timing in response to the fifth instruction.

In an embodiment, the contrast enhanced imaging method may further comprise: displaying at least one of the following control articles when the current data acquisition mode is the forward acquisition mode:

a control article for super-resolution configured to generate the third instruction after being clicked;

a control article for starting collection configured to generate the fourth instruction after being clicked;

a control article for ending collection configured to generate the fifth instruction after being clicked;

a control article for timer configured to start timing and displaying duration in response to the fourth instruction and to end timing in response to the fifth instruction; and a control article for quantitative analysis configured to generate the instruction for quantitative analysis after being clicked.

In accordance with a second aspect, a contrast enhanced imaging method provided in an embodiment may include:

determining a current data acquisition mode from a plurality of predetermined data acquisition modes, the plurality of predetermined data acquisition modes including a backward acquisition mode and a forward acquisition mode;

when the current data acquisition mode is the backward acquisition mode:

in response to a first transmission instruction, transmitting first ultrasonic waves at a first frame rate to a target tissue containing contrast micro-bubbles and receiving echo signals of the first ultrasonic waves to generate and display a first contrast enhanced image in real time based on the echo signals of the first ultrasonic waves;

displaying a first interface having a first control article for starting collection;

in response to a click operation on the first control article for starting collection, transmitting second ultrasonic waves at a second frame rate greater than the first frame rate to the target tissue containing contrast micro-bubbles and receiving echo signals of the second ultrasonic waves;

generating and displaying a second contrast enhanced image in real time based on the echo signals of the second ultrasonic waves; and generating and displaying a super-resolution image based on the echo signals of the second ultrasonic waves; and when the current data acquisition mode is the forward acquisition mode:

in response to a second transmission instruction, transmitting third ultrasonic waves at a third frame rate greater than the first frame rate to the target tissue containing contrast micro-bubbles and receiving echo signals of the third ultrasonic waves to generate and display a third contrast enhanced image in real time based on the echo signals of the third ultrasonic waves;

displaying a second interface having a control article for super-resolution;

freezing the third contrast enhanced image in response to a click operation on the control article for super-resolution; and generating and displaying a super-resolution image based on the echo signals of the third ultrasonic waves in a period of time before freezing.

In an embodiment, the first interface may further comprise at least one of the following control articles: a first control article for ending collection, a control article for timer and a control article for quantitative analysis; and the contrast enhanced imaging method may further comprise when the current data acquisition mode is the backward acquisition mode:

in response to a click operation on the first control article for ending collection, stopping transmitting the second ultrasonic waves and/or stopping receiving the echo signals of the second ultrasonic waves; and/or, in response to a click operation on the first control article for starting collection, controlling the control article for timer to start timing, and display duration for the received echo signals of the second ultrasonic waves; and/or, in response to a click operation on the control article for quantitative analysis, performing quantitative analysis on the super-resolution image, and displaying an analysis result of the quantitative analysis.

In an embodiment, the second interface may further comprise a second control article for starting collection and a second control article for ending collection; and generating and displaying a super-resolution image based on the echo signals of the third ultrasonic waves in a period of time before freezing may comprise:

displaying, in a data playback manner, an image generated by the echo signals of the third ultrasonic waves in a period of time before freezing;

in response to a click operation on the second control article for starting collection, determining a start point based on the generated image;

in response to a click operation on the second control article for ending collection, determining an end point based on the generated image; and determining the echo signals of the third ultrasonic waves corresponding to a duration between the start point and the end point from the echo signals of the third ultrasonic waves in a period of time before freezing, so as to generate the super-resolution image.

In an embodiment, the second interface may further comprise at least one of the following control articles: a control article for timer and a control article for quantitative analysis; and the contrast enhanced imaging method may further comprise when the current data acquisition mode is the backward acquisition mode:

in response to a click operation on the second control article for starting collection, controlling the control article for timer to start timing and display the duration, and in response to a click operation on the second control article for ending collection, controlling the control article for timer to end timing; and/or, in response to a click operation on the control article for quantitative analysis, performing quantitative analysis on the super-resolution image, and displaying an analysis result of the quantitative analysis.

In an embodiment, generating and displaying a second contrast enhanced image in real time based on the echo signals of the second ultrasonic waves may comprise: extracting partial frames from the echo signals of the second ultrasonic waves, and generating and displaying the second contrast enhanced image based on said partial frames; and generating and displaying a third contrast enhanced image in real time based on the echo signals of the third ultrasonic waves may comprise: extracting partial frames from the echo signals of the third ultrasonic waves, and generating and displaying the third contrast enhanced image based on said partial frames.

In an embodiment, generating and displaying a super-resolution image based on the echo signals of the second ultrasonic waves may comprise: performing super-resolution data processing on the echo signals of the second ultrasonic waves to obtain said super-resolution image; and generating and displaying a super-resolution image based on the echo signals of the third ultrasonic waves in a period of time before freezing may comprise: performing super-resolution data processing on the echo signals of the third ultrasonic waves in a period of time before freezing to obtain said super-resolution image.

In an embodiment, the super-resolution data processing may comprise:

extracting signals for contrast micro-bubbles from echo signals of ultrasonic waves to be processed;

separating the extracted signals for contrast micro-bubbles;

positioning each contrast micro-bubble;

tracking a trajectory of each contrast micro-bubble;

performing image construction based on the positioning and trajectory tracking of each contrast micro-bubble so as to obtain the super-resolution image.

In an embodiment, the contrast enhanced imaging method may further comprise: displaying progress of the super-resolution data processing while performing the super-resolution data processing.

In an embodiment, the contrast enhanced imaging method may further comprise: displaying the second contrast enhanced image and the super-resolution image on a same display interface when the current data acquisition mode is the backward acquisition mode; and/or, displaying the third contrast enhanced image and the super-resolution image on a same display interface when the current data acquisition mode is the forward acquisition mode.

In accordance with a third aspect, an ultrasonic imaging system provided in an embodiment may include:

an ultrasonic probe configured to transmit ultrasonic waves and receive echo signals of the ultrasonic waves;

a transmitting and receiving control circuit configured to control the ultrasonic probe to transmit the ultrasonic waves and receive the echo signals of the ultrasonic waves;

a processor configured to perform the method according to any one of the embodiments herein; and a display configured to display the super-resolution image.

According to the contrast enhanced imaging methods and ultrasonic imaging systems in the above embodiments, two data acquisition modes, backward acquisition mode and forward acquisition mode, are provided. In each mode, users can easily collect super-resolution imaging data, which is extremely convenient.

BRIEF DESCRIPTION OF THE DRAWINGS

FIG. 7 is a flowchart of a contrast enhanced imaging method in an embodiment;

FIG. 9 is a flowchart of a contrast enhanced imaging method in an embodiment; and FIG. 10 is a flowchart for generating and displaying a super-resolution image based on the echo signals of the third ultrasonic waves in a period of time before freezing in an embodiment.

DETAILED DESCRIPTION

Figure 1:
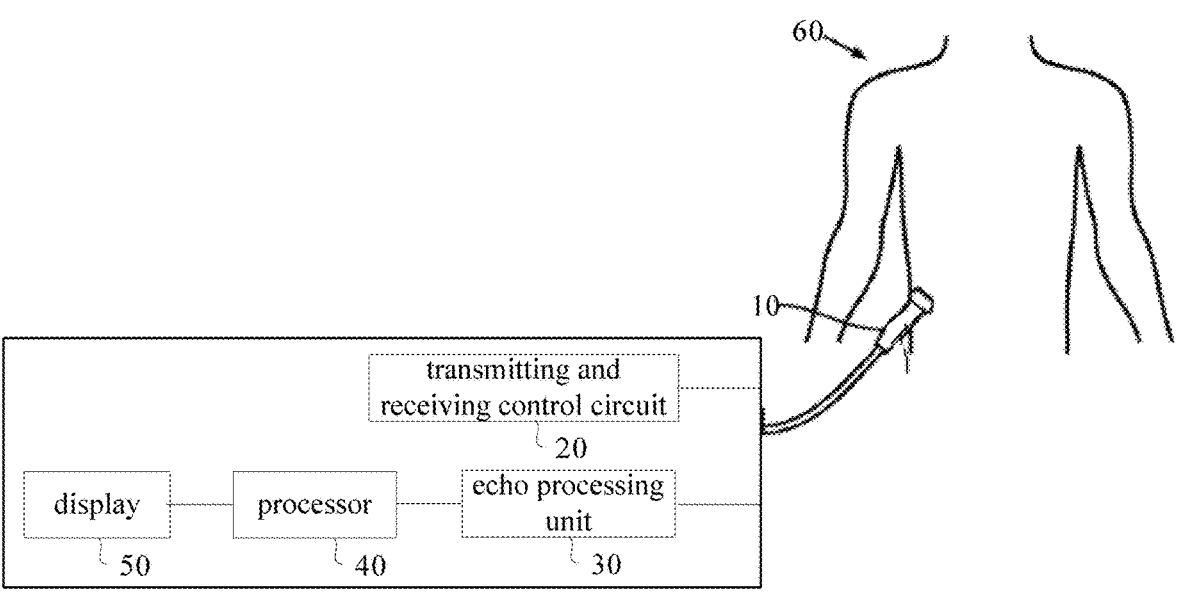
FIG. 1 is a schematic diagram of the structure of an ultrasonic imaging system in an embodiment.

The present disclosure will be further described in detail below through specific embodiments with reference to the accompanying drawings. Common or similar elements are referenced with like or identical reference numerals in different embodiments. Many details described in the following embodiments are for better understanding the present disclosure. However, those skilled in the art can realize with minimal effort that some of these features can be omitted in different cases or be replaced by other elements, materials and methods. For clarity some operations related to the present disclosure are not shown or illustrated herein so as to prevent the core from being overwhelmed by excessive descriptions. For those skilled in the art, such operations are not necessary to be explained in detail, and they can fully understand the related operations according to the description in the specification and the general technical knowledge in the art.

In addition, the features, operations or characteristics described in the specification may be combined in any suitable manner to form various embodiments. At the same time, the steps or actions in the described method can also be sequentially changed or adjusted in a manner that can be apparent to those skilled in the art. Therefore, the various sequences in the specification and the drawings are only for the purpose of describing a particular embodiment, and are not intended to be an order of necessity, unless otherwise stated one of the sequences must be followed.

The serial numbers of components herein, such as "first", "second", etc., are only used to distinguish the described objects and do not have any order or technical meaning. The terms "connected", "coupled" and the like here include direct and indirect connections (coupling) unless otherwise specified.

There are two main strategies for contrast-enhanced data acquisition of super-resolution at present. One is to collect data at conventional frame rate by diluting the concentration of contrast agent, but the collection time thereabout generally takes more than 20 minutes. The other is to shorten the collection time by increasing the frame rate of ultrasound image (for example, increasing to 500 frames per second). The present disclosure considers using ultra-high frame rate acquisition as the basis to shorten the time for data acquisition of super-resolution while providing a more convenient data acquisition scheme.

The present disclosure can be applied to ultrasonic imaging systems. Please refer to FIG. 1, an ultrasonic imaging system in an embodiment may include an ultrasonic probe 10, a transmitting and receiving control circuit 20, an echo processing unit 30 and a processor 40. In another embodiment, it may also include a display 50. Each component may be described in detail below.

The ultrasonic probe 10 may be configured to transmit ultrasonic waves and receive echo signals of the ultrasonic waves. In some specific embodiments, the ultrasonic probe 10 may include a plurality of array elements to achieve the mutual conversion of electrical pulse signals and the ultrasonic wave, so as to realize transmission of the ultrasonic waves to a biological tissue 60 (biological tissue in a human body or an animal body) under examination and reception of ultrasonic echoes reflected by the tissue to obtain echo signals of the ultrasonic waves. The array element can transmit the ultrasonic waves based on excitation electrical signals, or convert the received ultrasonic echoes into electrical signals. Therefore, each array element can be used to transmit the ultrasonic waves to a region of interest of the biological tissue, and can also be used to receive the echo signals returned by the tissue. During ultrasonic detection, it is possible to control, by a transmitting sequence and a receiving sequence, which array elements are used for transmission of the ultrasonic waves and which array elements are used for reception of the ultrasonic echoes, or to control the array elements to be used for transmitting the ultrasonic waves and receiving the ultrasonic echoes in time slots. All the array elements participating in transmission of the ultrasonic waves may be excited by electrical signals simultaneously, thereby transmitting the ultrasonic waves at the same time; alternatively, all the array elements participating in transmission of the ultrasonic waves may be excited by a number of electrical signals with a certain time interval, thereby continuously transmitting the ultrasonic waves with a certain time interval.

The transmitting and receiving control circuit 20 may be configured to control the ultrasonic probe 10 to transmit the ultrasonic waves and receive the echo signals of the ultrasonic waves. For example, the transmitting and receiving control circuit 20 may be used, on the one hand, to control the ultrasonic probe 10 to the biological tissues 60 (such as the region of interest thereof), and on the other hand, to control the ultrasonic probe 10 to receive the echo signals of the ultrasonic waves reflected by the tissue. In some specific embodiments, the transmitting and receiving control circuit 20 may be configured to generate the transmitting sequence and the receiving sequence, and output them to the ultrasonic probe 10. The transmitting sequence may be used to control some or all of the plurality of array elements in the ultrasonic probe 10 to transmit the ultrasonic waves to the biological tissue 60; and the parameters of the transmitting sequence may include the number of the array elements used for transmission and transmitting parameters of the ultrasonic waves (such as amplitude, frequency, number of waves transmitted, transmission interval, transmission angle, wave pattern, and/or focusing position, etc.). The receiving sequence may be used to control some or all of the plurality of the array elements to receive the ultrasonic echoes of the ultrasonic waves reflected by the tissue; and the parameters of the receiving sequence may include the number of the array elements used for reception and receiving parameters of the echoes (such as receiving angle, depth, etc.). The ultrasonic parameters in the transmitting sequence and the echo parameters in the receiving sequence vary depending on the purpose of the ultrasonic echoes or the image generated by the ultrasonic echoes.

A transmission frame rate or an imaging frame rate is related to a variety of parameters, such as the number of transmission, linear density, imaging range and pulse repetition frequency, etc. The number of transmission may refer to the number of sub-frames required to form a single image, and the pulse repetition frequency (PRF) may refer to the number of trigger pulses generated per second. One or more of the following may be adopted to improve the frame rate: reducing the number of transmission; decreasing the linear density; shortening the imaging range; and increasing PRF. Specifically, the number of transmission can be reduced by using plane-wave transmission techniques or coherence transmission synthesis (CTS) techniques in some examples; the linear density can be decreased while image quality is guaranteed in some examples; and the imaging range can be shortened after the completion of lesion localization in some examples. For example, specific regions of interest (ROI) can be selected after completing lesion localization to shorten the imaging range and/or increase the PRF.

The echo processing unit 30 may be configured to process the echo signals received by the ultrasonic probe 10, such as filtering, amplifying and beamforming the echo signals. In some specific embodiments, the echo processing unit 30 can output the processed signals or data to the processor 40; or it may store the processed signals or data in a memory first, and then read the echo signals or data from the memory when it is necessary to perform calculations based on the echo signals. It should be understood by those skilled in the art that in some embodiments, the echo processing unit 30 may be omitted when processes of the echo signals of the ultrasonic waves, including filtering, amplifying and beamforming, are not required.

The processor 40 may be configured to obtain ultrasonic echo data or signals, and use relevant algorithms to acquire required parameters or images. The processor 40 in some embodiments of the present disclosure may include means for interpreting computer instructions and processing data in computer software, such as, but not limited to, a central processing unit (CPU), a micro controller unit (MCU), a field-programmable gate array (FPGA) and a digital signal processor (DSP). In some embodiments, the processor 40 may be configured to execute various computer applications in a non-temporary computer-readable storage medium, thereby enabling a sample analysis device to perform a corresponding detection process.

It should be noted that the terms data and signal are sometimes used interchangeably herein and are not strictly distinguished.

The display 50 may be configured to display display information, such as displaying parameters and images acquired by the processor 40. It should be understood by those skilled in the art that, in some embodiments, the ultrasonic imaging system itself may not be integrated with a display unit, but rather be connected to a computer device (e.g., a PC) to display information via a display unit (e.g., a display screen) of the computer device. In some embodiments, the content displayed on the display 50 may also include a graphical interface that is offered to users for human-machine interaction and provided with one or more controlled objects, such that the users may input operation instructions via a human-machine interaction (HMI) device to control the controlled objects to perform corresponding control operations. In still some embodiments, the ultrasonic imaging system may also have other HMI devices in addition to the display 50, which are connected to the processor 40. For example, the processor 40 may be connected to the HMI device through an external input/output port, which may be a wireless communication unit, a wired communication unit, or a combination of the two. The external input/output port may also be implemented based on USB, bus protocols such as CAN, and/or wired network protocols.

The HMI device may include an input device configured to detect user input information, which may be, for example, a control instruction for the ultrasonic transmission/reception timing, an operational input instruction for drawing points, lines, or boxes on the ultrasonic image, or other instruction types. The input device may include one or any combination of the following: a keyboard, a mouse, a wheel, a trackball, a mobile input device (such as a mobile device with a touch screen, a mobile phone, etc.), a multi-function knob. The HMI device may also an include output device such as a printer.

The above are some explanations of the ultrasonic imaging system.

In some embodiments, a plurality of data acquisition modes are provided, such as a backward acquisition mode and a forward acquisition mode; and the processor 40 may determine a current data acquisition mode from the plurality of predetermined data acquisition modes. How to acquire data when the current data acquisition mode is the backward acquisition mode or when the current data acquisition mode is the forward acquisition mode are described respectively as follows.

1. Case Where the Current Data Acquisition Mode is the Backward Acquisition Mode.

In some embodiments, the processor 40 may, via the transmitting and receiving control circuit 20, control the ultrasonic probe 10 to transmit first ultrasonic waves at a first frame rate to a target tissue containing contrast micro-bubbles and receive the echo signals of the first ultrasonic waves. The processor 40 may generate a first contrast enhanced image in real time based on the echo signals of the first ultrasonic waves; and the display 50 may display the first contrast enhanced image.

The processor 40 may, in responses to a first instruction, via the transmitting and receiving control circuit 20, control the ultrasonic probe 10 to transmit second ultrasonic waves at a second frame rate to the target tissue containing contrast micro-bubbles, and receive the echo signals of the second ultrasonic waves. The second frame rate is greater than the first frame rate; and in some examples, it may be an ultra-high frame rate, such as over 100 frames per second. The first instruction here may be automatically generated by the ultrasonic imaging system (for example, the system may automatically generate the first instruction after determining that a preset condition is met), or it may be triggered by the users (for example, a relevant button may be clicked by the users to produce the first instruction; which will be further explained below. In some embodiments, in response to a second instruction, the processor 40 may, via the transmitting and receiving control circuit 20, control the ultrasonic probe 10 to stop transmitting second ultrasonic waves and/or receiving the echo signals of the second ultrasonic waves. Similarly, the second instruction here may be automatically generated by the ultrasonic imaging system (for example, the second instruction may be generated automatically by the system after determining that a preset condition, such as after a preset time, is met); or it may also be triggered by the users (for example, a relevant button may be clicked by the users to produce the second instruction). This will be further explained below.

In order to enable the users to know the acquisition progress of the super-resolution imaging data, in some embodiments, the display 50 may also display the duration for the received echo signals of the second ultrasonic waves.

The processor 40 may generate a second contrast enhanced image in real time based on the echo signals of the second ultrasonic waves. For example, the processor 40 may extract partial frames from the echo signals of the second ultrasonic waves and generate the second contrast enhanced image based on said partial frames; and the display 50 may display the second contrast enhanced image. In some embodiments, the processor 40 may, when extracting the partial frames from the echo signals of the second ultrasonic waves, extract the partial frames with the first frame rate from the echo signals of the second ultrasonic waves, so that the imaging frame rates of the two are equal.

In addition, the processor 50 may also generate a super-resolution image based on the echo signals of the second ultrasonic waves. For example, the processor 40 may perform super-resolution data processing on the echo signals of the second ultrasonic waves to obtain the super-resolution image. The display 50 may display the super-resolution image.

In order to enable the users to know the progress of data processing, in some embodiments, during the super-resolution data processing, the display 50 may also display the progress of super-resolution data processing, such as in the form of a progress bar.

In some embodiments, in response to an instruction for quantitative analysis, the processor 40 may perform quantitative analysis on the super-resolution image and display the analysis result of the quantitative analysis. In some embodiments, the quantitative analysis of the super-resolution image may include the quantitative analysis of vascular morphological parameters or hemodynamic parameters. The vascular morphological parameters may include vascular diameter, vascular density, vascular tortuosity, etc.; and the hemodynamic parameters may include average blood flow velocity, blood flow rate, etc. For example, the vascular morphological parameters such as vessel diameter, vascular density and vascular tortuosity may be obtained through image recognition and segmentation on the super-resolution image; and the hemodynamic parameters such as the average blood flow velocity and the blood flow rate may be obtained according to the velocity of micro-bubble movement. In some embodiments, the instruction for quantitative analysis may be generated automatically by the ultrasonic imaging system (for example, the instruction for quantitative analysis is generated automatically after determining that a preset condition is met, such as after a super-resolution image is generated), or it may be triggered by the users (for example, a relevant button may be clicked by the users to produce the instruction for quantitative analysis). This will be further explained below.

In some embodiments, the display 50 may display the second contrast enhanced image and the super-resolution image on the same display interface.

Figure 2:
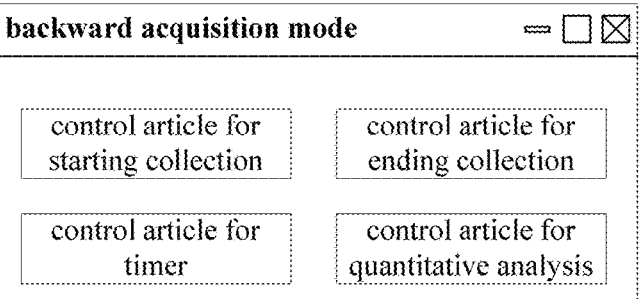
FIG. 2 is a schematic diagram of the control articles displayed under the backward acquisition mode in an embodiment.

In some embodiments, when the current data acquisition mode is the backward acquisition mode, the display 50 may display at least one of the following control articles: a control article for starting collection, a control article for ending collection, a control article for timer and a control article for quantitative analysis. FIG. 2 is an example. The control article for starting collection may be configured to generate the first instruction after being clicked in some embodiments. The control article for ending collection may be configured to generate the second instruction after being clicked in some embodiments. In some embodiments, the control article for starting collection and the control article for ending collection may be the same control which may generate the first instruction after being clicked, and then generate the second instruction after being clicked again. In yet some embodiments, the control article for timer may be configured to start timing in response to the first instruction, so as to display the duration such that the duration for the received echo signals of the second ultrasonic waves can be received. The control article for quantitative analysis may be configured to generate the instruction for quantitative analysis after being clicked in some embodiments.

These control articles may be displayed on, for example, the first interface, as shown in FIG. 2 above. It should be noted that the first interface may be displayed in the form of a pop-up window or in other forms, which is not limited here.

The above are some explanations of the backward acquisition mode.

2. Case Where the Current Data Acquisition Mode is the Forward Acquisition Mode.

In some embodiments, the processor 40 may, via the transmitting and receiving control circuit 20, control the ultrasonic probe 10 to transmit third ultrasonic waves to the target tissue containing contrast micro-bubbles and receive the echo signals of the third ultrasonic waves at a third frame rate. The third frame rate is greater than the first frame rate; and in some embodiments, it may be an ultra-high frame rate, such as over 100 frames per second. In some embodiments, the second frame rate may be the same to or different from the third frame rate.

The processor 40 may generate a third contrast enhanced image in real time based on the echo signals of the third ultrasonic waves, and the display 50 may display the third contrast enhanced image. For example, the processor 40 may extract partial frames from the echo signals of the third ultrasonic waves and generate the third contrast enhanced image based on the partial frames, and the display 50 may display the third contrast enhanced image. In some embodiments, the processor 40 may, when extracting the partial frames from the echo signals of the third ultrasonic waves, extract the partial frames from the echo signals of the third ultrasonic waves based on the first frame rate so that the imaging frame rates of the two are equal.

The generation principle and process of the contrast enhanced images (such as the first contrast enhanced image, the second contrast enhanced image and/or the third contrast enhanced image) mentioned herein may be as follows. By injecting a contrast agent (a solution containing contrast micro-bubbles) into the target tissue, it is possible to make the target tissue contain the contrast micro-bubbles. The echo property of the gas in the contrast micro-bubbles differs greatly from that of human tissue; therefore, the target tissue containing the contrast micro-bubbles may produce ultrasonic images with high contrast due to high difference in echo. The generation of contrast enhanced images may include extracting the echo component of the contrast agent from the echo signals of the ultrasonic waves while suppressing the echo components of the tissue; wherein different filters may be used to extract different signal components. The signal component generated by tissue reflection is the linear component in the echo signals, which reflects the structural characteristics of the tissue and is referred to as a tissue signal; and the signal component reflected by the contrast agent is the nonlinear component in the echo signal, which reflects the information of contrast agent micro-bubbles and is referred to as a contrast signal. By performing signal processing, such as demodulation, envelope finding and dynamic range transformation, on the linear and non-linear components respectively, a tissue reference image and a contrast enhanced image can be obtained. While displaying the contrast enhanced image, the tissue reference image may also be displayed on the display interface.

The processor 40 may, in response to a third instruction, freeze the third contrast enhanced image on the display 50; and the processor 40 may generate a super-resolution image based on the echo signals of the third ultrasonic waves in a period of time before freezing. For example, the processor may perform super-resolution data processing based on the echo signals of the third ultrasonic waves in a period of time before freezing to obtain the super-resolution image; and the display 50 may display the super-resolution image. The third instruction here may be generated automatically by the ultrasonic imaging system (for example, the third instruction is generated automatically after determining that a preset condition is met), or it may be triggered by the users (for example, a relevant button may be clicked by the users to produce the third instruction).

In some embodiment, the processor 40 generating the super-resolution image based on the echo signals of the third ultrasonic waves in a period of time before freezing may include that: the processor 40 controls the display 50 to display, in a data playback manner, an image generated by the echo signals of the third ultrasonic waves of a first time duration before freezing; the processor 40 determines a start point in response to the generated image and in response to a fourth instruction; the processor 40 determines an end point based on the generated image and in response to a fifth command; and the processor 40 determines the echo signals of the third ultrasonic waves between the start point and the end point from the echo signals of the third ultrasonic waves in a period of time before freezing to generate the aforesaid super-resolution image. The fourth instruction and the fifth instruction here may be generated automatically by the ultrasonic imaging system (for example, the fourth instruction and the fifth instruction are generated automatically after determining that a preset condition is met), or it may be triggered by the users (for example, a relevant button may be clicked by the users to produce the fourth instruction and the fifth instruction).

In order to enable the users to know the progress of data processing, in some embodiments, during the super-resolution data processing, the display 50 may also display the progress of super-resolution data processing, such as in the form of a progress bar.

In addition, a plurality of super-resolution data processing are involved herein. In an embodiment involving super-resolution data processing, referring to FIG. 3, the super-resolution data processing may include:

(1) Extracting signals for contrast micro-bubbles from the echo signals of the ultrasonic waves to be processed (such as the echo signals of the second ultrasonic waves, or the echo signals of the third ultrasonic waves in a period of time before freezing). For example, the process from A to B in FIG. 3 may represent the process of extracting signals for contrast micro-bubbles. The extraction of signals for contrast micro-bubbles is to separate the micro-bubbles from tissues. In some embodiments, the signals for contrast micro-bubbles can be extracted from the echo signals of the ultrasonic waves based on the nonlinear scattering characteristics of micro-bubbles, such as pulse reversal (PI), contrast pulse sequence (CPS), or super harmonic imaging. In some embodiments, the signals for contrast micro-bubbles can be extracted from the echo signals of the ultrasonic waves based on inter-frame differences caused by dissolution or rupture of micro-bubbles, such as differential imaging (DI). In some embodiments, the signals for contrast micro-bubbles can be extracted from the echo signals of the ultrasonic waves based on the flow characteristics of micro-bubbles, such as singular value decomposition (SVD) spatiotemporal filtering.

(2) Separating the extracted signals for contrast micro-bubbles. For example, the process from B to C in FIG. 3 may represent the separation of the extracted signals for contrast micro-bubbles. In some embodiments, the signals for contrast micro-bubbles may be processed by using bandpass filters of different frequencies, thereby distinguishing spatially overlapping contrast micro-bubbles in the frequency domain. In yet some embodiments, the signals for contrast micro-bubbles may be divided into multiple subsets based on the micro-bubble speed to achieve the reduction of the concentration of micro-bubbles.

(3) Localizing each contrast micro-bubble. For example, the process from C to D in FIG. 3 may represent the localization of each contrast micro-bubble. In some embodiments, a precise location of each contrast micro-bubble may be obtained through point diffusion function deconvolution by using centroid method.

(4) Tracking the trajectory of each contrast micro-bubble. For example, the process from D to E in FIG. 3 may represent the process of tracking the trajectory of each contrast micro-bubble. In some embodiments, after obtaining the precise location of each contrast micro-bubble, the trajectory of the contrast micro-bubble flowing with blood may be further tracked, thereby improving the fault tolerance of micro-bubble extraction and localization processing by pairing and tracking multiple frames.

Figure 3:
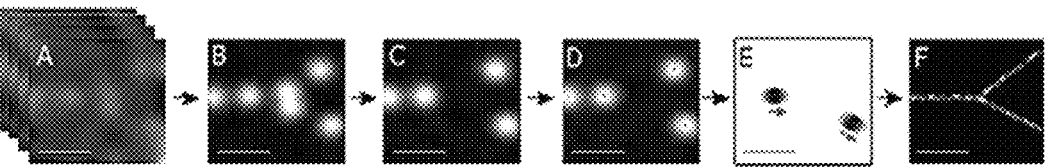
FIG. 3 is a schematic diagram of super-resolution data processing in an embodiment.

(5) performing image construction based on the localization and trajectory tracking of each contrast micro-bubble so as to obtain a super-resolution image (e.g., the F image shown in FIG. 3). In some embodiments, by locating and tracking the position of the centroid of micro-bubbles in microvascular flow imaging, as well as a period of accumulation and superimposition, a microvascular image with a "microscopic" effect is drawn to break through the original diffraction limit of ultrasonic waves and achieve the goal of super-resolution imaging that can distinguish micron-sized-vessels and their blood flow information, thereby achieving ultra-high resolution imaging of microvessels.

In some embodiments, the super-resolution image referred to herein may include a super-resolution velocity image, a super-resolution angle image and/or a super-resolution density-direction image, etc. The super-resolution velocity image is used to reflect the blood flow velocity of the microvessels and display the blood distribution of the microvessels. The super-resolution angle image can display the velocity direction of microvascular flow, in which different directions can be represented by different colors, a positive angle indicates the blood flowing to the ultrasonic probe, and a negative angle indicates the blood flowing away from the ultrasonic probe. The super-resolution density-direction image can be regarded as a super-resolution density image displayed in both directions, which can display the density of contrast micro-bubbles and blood flow direction simultaneously. For example, red represents flowing to the ultrasonic probe (upward flow), and the depth of red represents the density of the contrast micro-bubbles; while blue represents flowing away from the ultrasonic probe (downward flow), and the depth of blue represents the density of the contrast micro-bubbles.

In some embodiments, in response to an instruction for quantitative analysis, the processor 40 may perform quantitative analysis on the super-resolution image and display the analysis result of the quantitative analysis. In some embodiments, the quantitative analysis of the super-resolution image may include the quantitative analysis of vascular morphological parameters or hemodynamic parameters. The vascular morphological parameters may include vascular diameter, vascular density, vascular tortuosity, etc.; and the hemodynamic parameters may include average blood flow velocity, blood flow rate, etc. For example, the vascular morphological parameters such as vessel diameter, vascular density and vascular tortuosity may be obtained through image recognition and segmentation on the super-resolution image; and the hemodynamic parameters such as the average blood flow velocity and the blood flow rate may be obtained according to the velocity of micro-bubble movement. In some embodiments, the instruction for quantitative analysis may be generated automatically by the ultrasonic imaging system (for example, the instruction for quantitative analysis is generated automatically after determining that a preset condition is met, such as after a super-resolution image is generated), or it may be triggered by the users (for example, a relevant button may be clicked by the users to produce the instruction for quantitative analysis). This will be further explained below.

In some embodiments, the display 50 may display the second contrast enhanced image and the super-resolution image on the same display interface.

Figure 4:
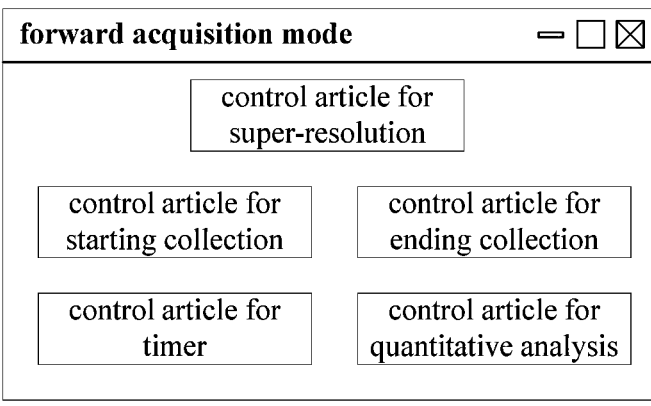
FIG. 4 is a schematic diagram of the control articles displayed under the forward acquisition mode in an embodiment.

In some embodiments, when the current data acquisition mode is the forward acquisition mode, the display 50 may display at least one of the following control articles: a control article for super-resolution, a control article for starting collection, a control article for ending collection, a control article for timer and a control article for quantitative analysis. FIG. 4 is an example. In some embodiments, the control article for super-resolution may be configured to generate the third instruction after being clicked. In some embodiments, the control article for starting collection may be configured to generate the fourth instruction after being clicked. In some embodiment, the control article for ending collection may be configured to generate the fifth command after being clicked. In some embodiments, the control article for starting collection and the control article for ending collection may be the same control which may generate the fourth instruction after being clicked and then generate the fifth instruction after being clicked again. In some embodiments, the control article for timer may start timing and display the duration in response to the fourth instruction, and may stop timing in response to the fifth instruction. In some embodiments, the control article for quantitative analysis may generate the instruction quantitative analysis after being clicked.

The above control articles may be displayed on, for example, a second interface. It should be noted that the second interface can be displayed in the form of a pop-up window or in other forms, which is not limited here.

The above are some explanations of the forward acquisition mode.

The ultrasonic imaging system according to the present disclosure provides two modes for user to choose from; and in each mode, super-resolution contrast enhanced data can be collected conveniently by the users. The following may take the first and second interfaces provided by the system to assist the users in the acquisition of super-resolution contrast enhanced data as an example to illustrate.

In some embodiments, the processor 40 may determine the current data acquisition mode from the plurality of predetermined data acquisition modes which may include the backward acquisition mode and the forward acquisition mode which may be associated with the first interface and the second interface respectively, and the display 50 may display the first interface under the backward acquisition mode and display the second interface under the forward acquisition mode.

Figure 5:
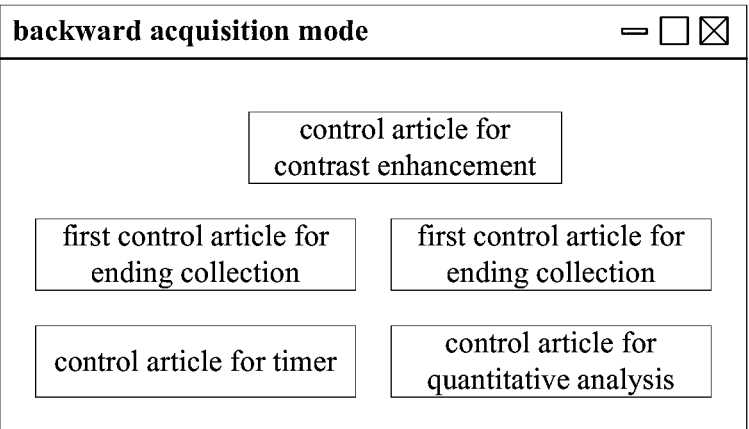
FIG. 5 is a schematic diagram of the first interface in an embodiment.
Figure 6:
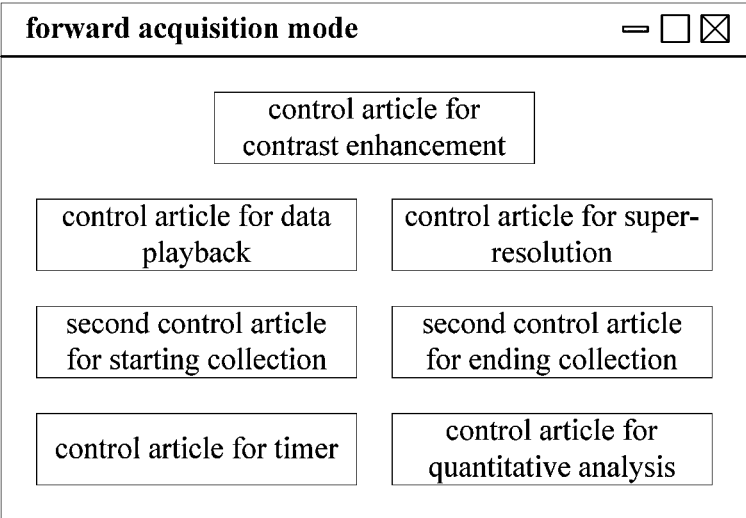
FIG. 6 is a schematic diagram of the second interface in an embodiment.

In some embodiments, the first interface may have a first control article for starting collection. In yet some embodiments, the first interface may further have at least one of the following control articles: a control article for contrast enhancement, a first control article for ending collection, a control article for timer and a control article for quantitative analysis. FIG. 5 is an example. In some embodiments, the second interface may have a control article for super-resolution. In still some embodiments, the second interface may also have at least one of the following control articles: a control article for contrast enhancement, a control article for data playback, a second control article for starting collection, a second control article for ending collection, a control article for timer and a control article for quantitative analysis. FIG. 6 is an example. The backward acquisition mode and the forward acquisition mode may be explained in conjunction with the first interface and the second interface respectively.

1. Case Where the Current Data Acquisition Mode is the Backward Acquisition Mode.

The processor 40 may, in response to a first transmission instruction, control the ultrasonic probe 10 via the transmitting and receiving control circuit 20 to transmit first ultrasonic waves to the target tissue containing contrast micro-bubbles at the first frame rate and receive the echo signals of the first ultrasonic waves. The processor 40 may generate the first contrast enhanced image in real time based on the echo signals of the first ultrasonic waves, and the display 50 may display the first contrast enhanced image. The first transmission instruction may be generated automatically generated by the ultrasonic imaging system, for example the system may automatically generate the first transmission instruction after determining that a preset condition is met. Alternatively, it may be triggered by the users, for example, a control article for contrast enhancement on the first interface may be clicked to produce the first transmission instruction.

In response to the click operation on the first control article for starting collection, the processor 40 may control the ultrasonic probe 10 via the transmitting and receiving control circuit 20 to transmit second ultrasonic waves to the target tissue containing contrast micro-bubbles at the second frame rate greater than the first frame rate and receive the echo signals of the second ultrasonic waves. The second frame rate is described above and will not be repeated here. In some embodiments, the processor 40 may, in response to the click operation on the first control article for starting collection, control the control article for timer on the first interface to start timing, and display the duration for the received echo signals of the second ultrasonic waves. In some embodiments, the processor 40 may, in response to the click operation on the first control article for ending collection, control the ultrasonic probe 10 via the transmitting and receiving control circuit 20 to stop transmitting second ultrasonic waves and/or to stop receiving the echo signals of the second ultrasonic waves.

The processor 40 may generate the second contrast enhanced image in real time based on the echo signals of the second ultrasonic waves. For example, the processor 40 may extract partial frames from the echo signals of the second ultrasonic waves and generate the second contrast enhanced image based on said partial frames. The display 50 may display the second contrast enhanced image. In some embodiments, the processor 40 may extract the partial frames from the echo signals of the second ultrasonic waves at the first frame rate when extracting the partial frames from the echo signals of the second ultrasonic waves so that the imaging frame rates of the two are equal.

In addition, the processor 40 may also generate the super-resolution image based on the echo signals of the second ultrasonic waves. For example, the processor 40 may perform super-resolution data processing on the echo signals of the second ultrasonic waves to obtain the super-resolution image. The display 50 may display the super-resolution image. In some embodiments, the display 50 may display the second contrast enhanced image and the super-resolution image on the same display interface.

In order to enable the users to know the progress of data processing, in some embodiments, during the super-resolution data processing, the display 50 may also display the progress of super-resolution data processing, such as in the form of a progress bar.

In some embodiments, the processor 40 may, in response to the click operation on the control article for quantitative analysis on the first interface, perform quantitative analysis on the super-resolution image and display the result of the quantitative analysis. In some embodiments, the quantitative analysis of the super-resolution image may include the quantitative analysis of vascular morphological parameters or hemodynamic parameters. The vascular morphological parameters may include vascular diameter, vascular density, vascular tortuosity, etc.; and the hemodynamic parameters may include average blood flow velocity, blood flow rate, etc. For example, the vascular morphological parameters such as vessel diameter, vascular density and vascular tortuosity may be obtained through image recognition and segmentation on the super-resolution image; and the hemodynamic parameters such as the average blood flow velocity and the blood flow rate may be obtained according to the velocity of micro-bubble movement.

An operation can be as follows:

After selecting the lesion to be observed, a user may click the control article for contrast enhancement on the first interface to initiate CEUS. After injecting a contrast agent into a human body at an appropriate time and determining that when a section and micro-bubble signal perfusion status meet a collection condition, the first control article for starting collection on the first interface may be clicked, then ultra-high frame rate data may be collected on the backend in real time and backward, and the control article for timer on the first interface may also be enabled for timing. In order to facilitate the user to determine the acquisition time, the display of a conventional contrast image can be achieved by extracting partial echo signals. After the first control article for ending collection on the first interface is clicked, the collection of ultra-high frame rate data will be ended on the backend, and the control article for timer will also stop timing. After the acquisition of the ultra-high frame rate data is completed, the system can automatically calculate offline; and a progress bar for calculation may be displayed during the calculation process, which is convenient for users to estimate the time for drawing. After the calculation is completed, the conventional contrast image and/or super-resolution images may be shown on an interface imaging area of the system.

The above are some explanations of the backward acquisition mode.

2. Case Where the Current Data Acquisition Mode is the Forward Acquisition Mode.

The processor 40 may, in response to the second transmission instruction, control the ultrasonic probe 10 via the transmitting and receiving control circuit 20, to transmit third ultrasonic waves to the target tissue containing contrast micro-bubbles at the third frame rate greater than the first frame rate and receive the echo signals of the third ultrasonic waves. The third frame rate is described above and will not be repeated here. The second transmission instruction may be generated automatically generated by the ultrasonic imaging system, for example the system may automatically generate the first instruction after determining that a preset condition is met. Alternatively, it may be triggered by the users, for example, a control article for contrast enhancement on the second interface may be clicked to produce the second transmission instruction.

The processor 40 may generate the third contrast enhanced image in real time based on the echo signals of the third ultrasonic waves, and the display 50 may display the third contrast enhanced image. For example, the processor 40 may extract partial frames from the echo signals of the third ultrasonic waves and generate the third contrast enhanced image based on said partial frames; and the display 50 may display the third contrast enhanced image. In some embodiments, the processor 40 may extract partial frames from the echo signals of the third ultrasonic waves at the first frame rate when extracting the partial frames from the echo signals of the third ultrasonic waves so that the imaging frame rates of the two are equal.

The processor 40 may freeze the third contrast enhanced image on the display 50 in response to the click operation of the control article for super-resolution; and the processor 40 may generate the super-resolution image based on the echo signals of the third ultrasonic waves in a period of time before freezing. For example, the processor 40 may perform super-resolution data processing on the echo signals of the third ultrasonic waves in a period of time before freezing to obtain the super-resolution image, and the display 50 may display the super-resolution image. In some embodiments, the display 50 may display the third contrast enhanced image and the super-resolution image on the same display interface.

In some specific embodiments, the processor 40 may control the display 50 to display, in a data playback manner, the image generated based on the echo signals of the third ultrasonic waves of a first time duration before freezing—for example, the processor 40 may control to perform data playback in response to the click operation of the control article for data playback. In response to the click operation on the second control article for starting collection on the second interface, the processor 40 may determine a start point based on the generated image; and in response to the click operation on the second control article for ending collection on the second interface, the processor 40 may determine an end point based on the generated image. Then the processor 40 may determine the echo signals of the third ultrasonic waves corresponding to the time duration between the start point and the end point based on the echo signals of the third ultrasonic waves in a period of time before freezing, so as to generate the super-resolution image. In some embodiments, the processor 40 may control the control article for timer on the second interface to start timing and display the duration in response to the click operation on the second control article for starting collection on the second interface, and may control the control article for timer on the second interface to stop timing in response to the click operation on the second control article for ending collection on the second interface.

In order to enable the users to know the progress of data processing, in some embodiments, during the super-resolution data processing, the display 50 may also display the progress of super-resolution data processing, such as in the form of a progress bar.

In some embodiments, the processor 40 may, in response to the click operation on the control article for quantitative analysis on the first interface, perform quantitative analysis on the super-resolution image and display the result of the quantitative analysis. In some embodiments, the quantitative analysis of the super-resolution image may include the quantitative analysis of vascular morphological parameters or hemodynamic parameters. The vascular morphological parameters may include vascular diameter, vascular density, vascular tortuosity, etc.; and the hemodynamic parameters may include average blood flow velocity, blood flow rate, etc. For example, the vascular morphological parameters such as vessel diameter, vascular density and vascular tortuosity may be obtained through image recognition and segmentation on the super-resolution image; and the hemodynamic parameters such as the average blood flow velocity and the blood flow rate may be obtained according to the velocity of micro-bubble movement.

An operation can be as follows:

After selecting the lesion to be observed, a user may click the control article for contrast enhancement on the second interface to initiate CEUS; and scanning with an ultra-high frame rate (e.g., the third frame rate mentioned above) may be launched on the backend under such mode. After a contrast agent is injected into a human body and the control article for super-resolution of the second interface is clicked at an appropriate time, the scanning with the ultra-high frame rate may be stopped, the image produced may be frozen at the moment, and the signals or data of a time of period before this moment may be stored in a memory. The control article for data playback on the second interface may be clicked by the user such that the data may be played in a playback manner by the system. The second control article for starting collection on the second interface may be clicked by the user based on the data played in a playback manner, then a start point may be determined on the backend and the control article for timer on the second interface may start timing at the same time. The second control article for ending collection on the second interface may be clicked such that an end point may be determined on the backend and the control article for timer on the second interface may stop timing simultaneously. The data between the start point and the end point may be regarded as the super-resolution data by the system. The system can automatically calculate offline; and a progress bar for calculation may be displayed during the calculation process, which is convenient for users to estimate the time for drawing. After the calculation is completed, the conventional contrast image and/or super-resolution images may be shown on the interface imaging area of the system.

The above are some explanations of the forward acquisition mode.

A contrast enhanced imaging method may be provided in an embodiment of the present disclosure, which will be described specifically below.

Please referring to FIG. 7, the contrast enhanced imaging method in an embodiment may include the following steps.

Step 100: determining the current data acquisition mode from a plurality of predetermined data acquisition modes; wherein the plurality of predetermined data acquisition modes may include the backward acquisition mode and the forward acquisition mode.

(1) Case Where the Current Data Acquisition Mode is the Backward Acquisition Mode Step 110: transmitting, at a first frame rate, first ultrasonic waves to a target tissue containing contrast micro-bubbles and receiving the echo signals of the first ultrasonic waves to generate and display a first contrast enhanced image in real time based on the echo signals of the first ultrasonic waves.

Step 111: in response to a first instruction, transmitting, at a second frame rate greater than the first frame rate, second ultrasonic waves to the target tissue containing contrast micro-bubbles and receiving the echo signals of the second ultrasonic waves. In some embodiments, step 111 may further include: in response to a second instruction, stopped transmitting the second ultrasonic waves and/or stopped receiving the echo signals of the second ultrasonic waves. In some embodiments, the second frame rate may be an ultra-high frame rate, such as over 100 frames per second. In order to enable the users to know the acquisition progress of the super-resolution imaging data, the contrast enhanced imaging method in some embodiments may further include: displaying the duration for the received echo signals of the second ultrasonic waves.

Step 112: generating and displaying the second contrast enhanced image in real time based on the echo signals of the second ultrasonic waves. In some embodiments, in step 112, partial frames may be extracted from the echo signals of the second ultrasonic waves, and the second contrast enhanced image may be generated and displayed based on said partial frames. In some embodiments, in step 112, when extracting the partial frames from the echo signals of the second ultrasonic waves, the partial frames may be extracted from the echo signals of the second ultrasonic waves at the first frame rate, so that the imaging frame rates of the two are equal.

Step 113: generating and displaying the super-resolution image based on the echo signals of the second ultrasonic waves. In some embodiments, in step 113, super-resolution data processing may be performed on the echo signals of the second ultrasonic waves; and in yet some embodiments, the second contrast enhanced image and the super-resolution image may be displayed on the same display interface.

In order to enable the users to know the progress of data processing, the contrast enhanced imaging method in some embodiments may further include: displaying the progress of the super-resolution data processing such as in form of a progress bar during the super-resolution data processing.

In some embodiments, in response to an instruction quantitative analysis, the super-resolution image may be performed with quantitative analysis and the result of the quantitative analysis may be displayed in step 114. In some embodiments, the quantitative analysis of the super-resolution image may include the quantitative analysis of vascular morphological parameters or hemodynamic parameters. The vascular morphological parameters may include vascular diameter, vascular density, vascular tortuosity, etc.; and the hemodynamic parameters may include average blood flow velocity, blood flow rate, etc. For example, the vascular morphological parameters such as vessel diameter, vascular density and vascular tortuosity may be obtained through image recognition and segmentation on the super-resolution image; and the hemodynamic parameters such as the average blood flow velocity and the blood flow rate may be obtained according to the velocity of micro-bubble movement. In some embodiments, the instruction for quantitative analysis may be generated automatically by the ultrasonic imaging system (for example, the instruction for quantitative analysis is generated automatically after determining that a preset condition is met, such as after a super-resolution image is generated), or it may be triggered by the users (for example, a relevant button may be clicked by the users to produce the instruction for quantitative analysis).

In a case where the current data acquisition mode is the backward acquisition mode, the contrast enhanced imaging in some embodiments may further include displaying at least one of the following control articles: a control article for starting collection, a control article for ending collection, a control article for timer and a control article for quantitative analysis. FIG. 2 is an example. In some embodiments, the control article for starting collection may be configured to generate the first instruction after being clicked. The control article for ending collection may be configured to generate the second instruction after being clicked in some embodiments. In some embodiments, the control article for starting collection and the control article for ending collection may be the same control which may generate the first instruction after being clicked, and then generate the second instruction after being clicked again. In yet some embodiments, the control article for timer may be configured to start timing in response to the first instruction, so as to display the duration such that the duration for the received echo signals of the second ultrasonic waves can be received. The control article for quantitative analysis may be configured to generate the instruction for quantitative analysis after being clicked in some embodiments.

(2) Case Where the Current Data Acquisition Mode is the Forward Acquisition Mode Step 120: transmitting third ultrasonic waves at a third frame rate greater than the first frame rate to the target tissue containing contrast micro-bubbles and receiving the echo signals of the third ultrasonic waves to generate and display a third contrast enhanced image in real time based on the echo signals of the third ultrasonic waves. In some embodiments, in step 120, partial frames may be extracted from the echo signals of the third ultrasonic waves and the third contrast enhanced image may be generated and displayed based on the partial frames. In some embodiments, in step 120, when extracting the partial frames from the echo signals of the third ultrasonic waves, the partial frames may be extracted from the echo signals of the third ultrasonic waves at the first frame rate so that the imaging frame rates of the two are equal.

Step 121: freezing the third contrast enhanced image in response to a third instruction.

Step 122: generating and displaying a super-resolution image based on the echo signals of the third ultrasonic waves in a period of time before freezing. In some embodiments, the third contrast enhanced image and the super-resolution image may be displayed on the same display interface. In some embodiments, in step 122, super-resolution data processing may be performed on the echo signals of the third ultrasonic waves in a period of time before freezing to obtain the super-resolution image.

In order to enable the users to know the progress of data processing, the contrast enhanced imaging method in an embodiment may further include: displaying the progress of the super-resolution data processing such as in form of a progress bar during the super-resolution data processing.

Figure 8:
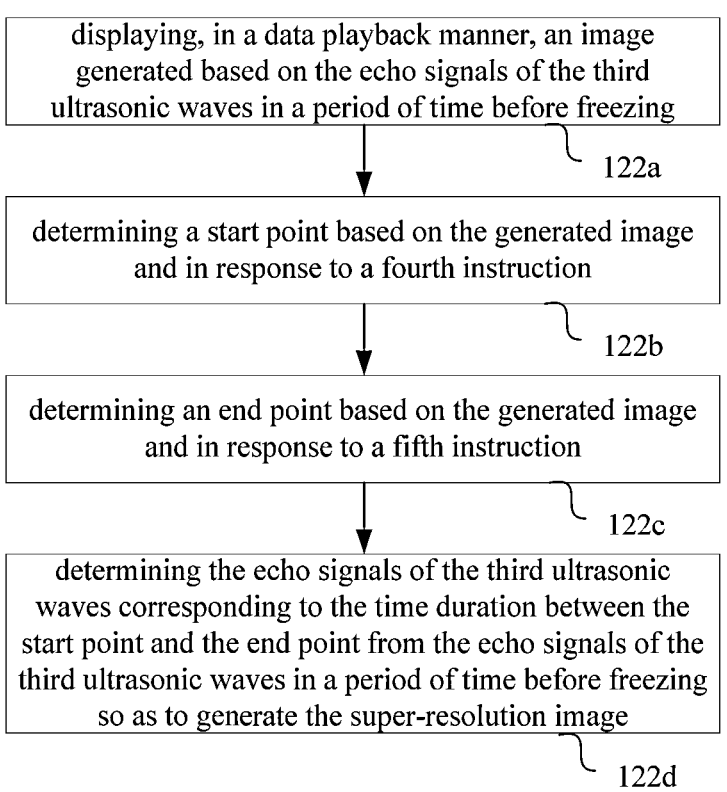
FIG. 8 is a flowchart for generating and displaying a super-resolution image based on the echo signals of the third ultrasonic waves in a period of time before freezing in an embodiment.

Please referring to FIG. 8. In some embodiments, the generation and display of a super-resolution image based on the echo signals of the third ultrasonic waves in a period of time before freezing in step 122 may include the following steps:

Step 122a: displaying, in a data playback manner, an image generated based on the echo signals of the third ultrasonic waves in a period of time before freezing;

Step 122b: determining a start point based on the generated image and in response to a fourth instruction;

Step 122c: determining an end point based on the generated image and in response to a fifth instruction; and Step 122d: determining the echo signals of the third ultrasonic waves corresponding to the time duration between the start point and the end point from the echo signals of the third ultrasonic waves in a period of time before freezing so as to generate the super-resolution image.

In some embodiments, in response to an instruction for quantitative analysis, the super-resolution image may be performed with quantitative analysis and the result of the quantitative analysis may be displayed in step 123. In some embodiments, the quantitative analysis of the super-resolution image may include the quantitative analysis of vascular morphological parameters or hemodynamic parameters. The vascular morphological parameters may include vascular diameter, vascular density, vascular tortuosity, etc.; and the hemodynamic parameters may include average blood flow velocity, blood flow rate, etc. For example, the vascular morphological parameters such as vessel diameter, vascular density and vascular tortuosity may be obtained through image recognition and segmentation on the super-resolution image; and the hemodynamic parameters such as the average blood flow velocity and the blood flow rate may be obtained according to the velocity of micro-bubble movement. In some embodiments, the instruction for quantitative analysis may be generated automatically by the ultrasonic imaging system (for example, the instruction for quantitative analysis is generated automatically after determining that a preset condition is met, such as after a super-resolution image is generated), or it may be triggered by the users (for example, a relevant button may be clicked by the users to produce the instruction for quantitative analysis).

In a case where the current data acquisition mode is the forward acquisition mode, the contrast enhanced imaging in some embodiments may further include displaying at least one of the following control articles: a control article for super-resolution, a control article for starting collection, a control article for ending collection, a control article for timer and a control article for quantitative analysis. FIG. 4 is an example. In some embodiments, the control article for super-resolution may be configured to generate the third instruction after being clicked. In some embodiments, the control article for starting collection may be configured to generate the fourth instruction after being clicked. In some embodiment, the control article for ending collection may be configured to generate the fifth command after being clicked. In some embodiments, the control article for starting collection and the control article for ending collection may be the same control which may generate the fourth instruction after being clicked and then generate the fifth command after being clicked again. In some embodiments, the control article for timer may start timing and display the duration in response to the fourth instruction, and may stop timing in response to the fifth instruction. In some embodiments, the control article for quantitative analysis may generate the instruction for quantitative analysis after being clicked.

Please referring to FIG. 9, the contrast enhanced imaging method in an embodiment may include the following steps.

Step 200: determining the current data acquisition mode from a plurality of predetermined data acquisition modes; wherein the plurality of predetermined data acquisition modes may include the backward acquisition mode and the forward acquisition mode.

(1) Case Where the Current Data Acquisition Mode is the Backward Acquisition Mode Step 210: in response to a first transmission instruction, transmitting first ultrasonic waves to a target tissue containing contrast micro-bubbles at a first frame rate and receiving the echo signals of the first ultrasonic waves to generate and display a first contrast enhanced image in real time based on the echo signals of the first ultrasonic waves.

Step 211: displaying a first interface having a first control article for starting collection. In some embodiments, the first interface may further include at least one of the following control articles: a control article for contrast enhancement, a first control article for ending collection, a control article for timer and a control article for quantitative analysis. FIG. 5 is an example.

Step 212: in response to a click operation on the first control article for starting collection, transmitting second ultrasonic waves at a second frame rate greater than the first frame rate to the target tissue containing contrast micro-bubbles and receiving the echo signals of the second ultrasonic waves. In some embodiments, in response to the click operation on the first control article for starting collection, the step 212 may further include: controlling the control article for timer on the first interface to start timing, and displaying the duration for the received echo signals of the second ultrasonic waves. In some embodiments, in response to the click operation of the first control article for ending collection, the step 212 may further include: stopping transmitting the second ultrasonic waves and/or stopping receiving the echo signals of the second ultrasonic waves.

Step 213: generating and displaying a second contrast enhanced image in real time based on the echo signals of the second ultrasonic waves. In some embodiments, partial frames may be extracted from the echo signals of the second ultrasonic waves and the second contrast enhanced image may be generated and displayed based on said partial frames in step 213. In some embodiments, when extracting the partial frames from the echo signals of the second ultrasonic waves, the partial frames may be extracted from the echo signals of the second ultrasonic waves based on the first frame rate so that the imaging frame rates of the two are equal in step 213.

Step 214: generating and displaying a super-resolution image based on the echo signals of the second ultrasonic waves. In some embodiments, the echo signals of the second ultrasonic waves may be performed with super-resolution data processing to obtain the super-resolution image in step 214. In some embodiments, the second contrast enhanced image and the super-resolution image may be displayed on the same display interface.

In order to enable the users to know the progress of data processing, the contrast enhanced imaging method in some embodiments may further include: displaying the progress of the super-resolution data processing such as in form of a progress bar during the super-resolution data processing.

In some embodiments, in step 215, in response to the click operation on the control article for quantitative analysis on the first interface, the super-resolution image may be performed with quantitative analysis and the result of the quantitative analysis may be displayed. In some embodiments, the quantitative analysis of the super-resolution image may include the quantitative analysis of vascular morphological parameters or hemodynamic parameters. The vascular morphological parameters may include vascular diameter, vascular density, vascular tortuosity, etc.; and the hemodynamic parameters may include average blood flow velocity, blood flow rate, etc. For example, the vascular morphological parameters such as vessel diameter, vascular density and vascular tortuosity may be obtained through image recognition and segmentation on the super-resolution image; and the hemodynamic parameters such as the average blood flow velocity and the blood flow rate may be obtained according to the velocity of micro-bubble movement.

(2) Case Where the Current Data Acquisition Mode is the Forward Acquisition Mode Step 220: in response to a second transmission instruction, transmitting third ultrasonic waves at a third frame rate greater than the first frame rate to the target tissue containing contrast micro-bubbles and receiving the echo signals of the third ultrasonic waves to generate and display a third contrast enhanced image in real time based on the echo signals of the third ultrasonic waves. In some embodiments, partial frames may be extracted from the echo signals of the third ultrasonic waves and the third contrast enhanced image may be generated and displayed based on said partial frames in step 220. In some embodiments, when extracting the partial frames from the echo signals of the third ultrasonic waves, the partial frames may be extracted from the echo signals of the third ultrasonic waves based on the first frame rate so that the imaging frame rates of the two are equal in step 220.

Step 221: displaying a second interface having a control article for super-resolution. In some embodiments, the second interface may further include at least one of the following control articles: a control article for contrast enhancement, a control article for data playback, a second control article for starting collection, a second control article for ending collection, a control article for timer and a control article for quantitative analysis. FIG. 6 is an example.

Step 222: freezing the third contrast enhanced image in response to the click operation on the control article for super-resolution.

Step 223: generating and displaying the super-resolution image based on the echo signals of the third ultrasonic waves in a period of time before freezing. In some embodiments, the third contrast enhanced image and the super-resolution image may be displayed at the same display interface. In some embodiments, the super-resolution image may be obtained by performing super-resolution data processing on the echo signals of the third ultrasonic waves of the period of time before freezing.

In order to enable the users to know the progress of data processing, the contrast enhanced imaging method in some embodiments may further include: displaying the progress of the super-resolution data processing such as in form of a progress bar during the super-resolution data processing.

Please referring to FIG. 10. In some embodiments, the generation and display of a super-resolution image based on the echo signals of the third ultrasonic waves in a period of time before freezing in step 223 may include the following steps:

Step 223*a*: displaying, in a data playback manner, an image generated based on the echo signals of the third ultrasonic waves in a period of time before freezing;

Step 223*b*: in response to a click operation on the second control article for starting collection, determining a start point based on the generated image;

Step 223*c*: in response to a click operation on the second control article for ending collection, determining an end point based on the generated image; and Step 223*d*: determining the echo signals of the third ultrasonic waves corresponding to the time duration between the start point and the end point from the echo signals of the third ultrasonic waves in a period of time before freezing so as to generate the super-resolution image.

In some embodiments, in response to the click operation on the second control article for starting collection on the second interface, the control article for timer on the second interface may be controlled to start timing and the duration may be displayed in step 223*c;* and in response to the click operation on the second control article for ending collection on the second interface, the control article for timer on the second interface may be controlled to stop timing in step 223*c.*

In order to enable the users to know the progress of data processing, during super-resolution data processing, it may further include in some embodiments: displaying the progress of the super-resolution data processing such as in form of a progress bar.

In some embodiments, in step 224, in response to the click operation on the control article for quantitative analysis on the first interface, the super-resolution image may be performed with quantitative analysis and the result of the quantitative analysis may be displayed. In some embodiments, the quantitative analysis of the super-resolution image may include the quantitative analysis of vascular morphological parameters or hemodynamic parameters. The vascular morphological parameters may include vascular diameter, vascular density, vascular tortuosity, etc.; and the hemodynamic parameters may include average blood flow velocity, blood flow rate, etc. For example, the vascular morphological parameters such as vessel diameter, vascular density and vascular tortuosity may be obtained through image recognition and segmentation on the super-resolution image; and the hemodynamic parameters such as the average blood flow velocity and the blood flow rate may be obtained according to the velocity of micro-bubble movement.

The present disclosure is illustrated with reference to various exemplary embodiments. However, those skilled in the art may recognize that the exemplary embodiments can be changed and modified without departing from the scope of the present disclosure. For example, various operation steps and components used to execute the operation steps may be implemented in different ways (for example, one or more steps may be deleted, modified, or combined into other steps) according to specific application(s) or any number of cost functions associated with the operation of the system.

In the above embodiments, it can be fully or partially implemented through software, hardware, firmware, or any combination thereof. In addition, as understood by those skilled in the art, the principles herein may be reflected in a computer program product on a computer-readable storage medium that is preloaded with computer-readable program code. Any tangible, non-temporary computer-readable storage medium can be used, including magnetic storage devices (hard disks, floppy disks, etc.), optical storage devices (CD-ROMs, DVDs, Blu Ray disks, etc.), flash memory and/or the like. The computer program instructions may be loaded onto a general purpose computer, a special purpose computer, or other programmable data processing device to form a machine, so that these instructions executed on a computer or other programmable data processing device can form a device that realizes a specified function. These computer program instructions may also be stored in a computer-readable memory that can instruct a computer or other programmable data processing device to run in a specific way, so that the instructions stored in the computer-readable memory can form a manufacturing product, including a realization device to achieve a specified function. The computer program instructions may also be loaded onto a computer or other programmable data processing device to execute a series of operating steps on the computer or other programmable device to produce a computer-implemented process, so that instructions executed on the computer or other programmable device can provide steps for implementing a specified function.

What is claimed is:

1. A contrast enhanced imaging method, comprising:

determining a current data acquisition mode from a plurality of predetermined data acquisition modes, wherein the plurality of predetermined data acquisition modes includes a backward acquisition mode and a forward acquisition mode;

when the current data acquisition mode is the backward acquisition mode, the method further comprises:

transmitting first ultrasonic waves at a first frame rate to a target tissue containing contrast micro-bubbles and receiving echo signals of the first ultrasonic waves to generate and display a first contrast enhanced image in real time based on the echo signals of the first ultrasonic waves;

in response to a first instruction, transmitting second ultrasonic waves at a second frame rate greater than the first frame rate to the target tissue containing contrast micro-bubbles and receiving echo signals of the second ultrasonic waves to generate and display a second contrast enhanced image in real time based on the echo signals of the second ultrasonic waves; and generating and displaying a super-resolution image based on the echo signals of the second ultrasonic waves; and when the current data acquisition mode is the forward acquisition mode, the method further comprises:

transmitting third ultrasonic waves at a third frame rate greater than the first frame rate to the target tissue containing contrast micro-bubbles and receiving echo signals of the third ultrasonic waves to generate and display a third contrast enhanced image in real time based on the echo signals of the third ultrasonic waves;

in response to a third instruction, freezing the third contrast enhanced image; and generating and displaying a super-resolution image, based on the echo signals of the third ultrasonic waves in a period of time before freezing.

2. The contrast enhanced imaging method according to claim 1, wherein generating and displaying a second contrast enhanced image in real time based on the echo signals of the second ultrasonic waves comprises: extracting partial frames from the echo signals of the second ultrasonic waves, and generating and displaying the second contrast enhanced image based on said partial frames; and wherein generating and displaying a third contrast enhanced image in real time based on the echo signals of the third ultrasonic waves comprises: extracting partial frames from the echo signals of the third ultrasonic waves, and generating and displaying the third contrast enhanced image based on said partial frames.

3. The contrast enhanced imaging method according to claim 1, wherein generating and displaying a super-resolution image based on the echo signals of the second ultrasonic waves comprises: performing super-resolution data processing on the echo signals of the second ultrasonic waves to obtain said super-resolution image; and generating and displaying a super-resolution image based on the echo signals of the third ultrasonic waves in a period of time before freezing comprises: performing super-resolution data processing on the echo signals of the third ultrasonic waves in a period of time before freezing to obtain said super-resolution image.

4. The contrast enhanced imaging method according to claim 1, further comprising: displaying progress of the super-resolution data processing while performing the super-resolution data processing.

5. The contrast enhanced imaging method according to claim 1, further comprising: in response to an instruction for quantitative analysis, performing quantitative analysis on the super resolution image, and displaying an analysis result of the quantitative analysis.

6. The contrast enhanced imaging method according to claim 1, further comprising at least one of:

displaying the second contrast enhanced image and the super-resolution image on a same display interface when the current data acquisition mode is the backward acquisition mode; and displaying the third contrast enhanced image and the super-resolution image on a same display interface when the current data acquisition mode is the forward acquisition mode.

7. The contrast enhanced imaging method according to claim 1, further comprising: displaying a duration for the received echo signals of the second ultrasonic waves when the current data acquisition mode is the backward acquisition mode.

8. The contrast enhanced imaging method according to claim 7, further comprising: displaying at least one of following control articles when the current data acquisition mode is the backward acquisition mode:

a control article for starting collection configured to generate the first instruction after being clicked, wherein the starting collection refers to transmitting the second ultrasonic waves at the second frame rate greater than the first frame rate to the target tissue containing the contrast micro-bubbles and receiving the echo signals of the second ultrasonic waves;

a control article for ending collection configured to generate a second instruction after being clicked, the second instruction being used to stop transmitting the second ultrasonic waves and/or stop receiving the echo signals of the second ultrasonic waves, wherein the ending collection refers to stopping transmitting the second ultrasonic waves at the second frame rate greater than the first frame rate to the target tissue containing the contrast micro-bubbles and stopping receiving the echo signals of the second ultrasonic waves;

a control article for timer configured to start timing in response to the first instruction, so as to display the duration; and a control article for quantitative analysis configured to generate the instruction for quantitative analysis after being clicked.

9. The contrast enhanced imaging method according to claim 1, wherein generating and displaying a super-resolution image based on the echo signals of the third ultrasonic waves in a period of time before freezing comprises:

displaying, in a data playback manner, an image generated by the echo signals of the third ultrasonic waves in a period of time before freezing;

determining a start point based on the generated image and in response to a fourth instruction;

determining an end point based on the generated image and in response to a fifth instruction; and determining the echo signals of the third ultrasonic waves corresponding to a duration between the start point and the end point from the echo signals of the third ultrasonic waves in a period of time before freezing, so as to generate the super-resolution image.

10. The contrast enhanced imaging method according to claim 9, further comprising: starting timing and displaying duration in response to the fourth instruction, and ending timing in response to the fifth instruction.

11. The contrast enhanced imaging method according to claim 10, further comprising: displaying at least one of following control articles when the current data acquisition mode is the forward acquisition mode:

a control article for super-resolution configured to generate the third instruction after being clicked;

a control article for starting collection configured to generate the fourth instruction after being clicked, wherein the starting collection refers to a start point of the echo signals of the third ultrasonic waves in the period of time before freezing;

a control article for ending collection configured to generate the fifth instruction after being clicked, wherein the ending collection refers to an ending point of the echo signals of the third ultrasonic waves in the period of time before freezing;

a control article for timer configured to start timing and display the duration in response to the fourth instruction and to end timing in response to the fifth instruction; and a control article for quantitative analysis configured to generate the instruction for quantitative analysis after being clicked.

12. A contrast enhanced imaging method, comprising:

determining a current data acquisition mode from a plurality of predetermined data acquisition modes, wherein the plurality of predetermined data acquisition modes including a backward acquisition mode and a forward acquisition mode;

when the current data acquisition mode is the backward acquisition mode:

in response to a first transmission instruction, transmitting first ultrasonic waves at a first frame rate to a target tissue containing contrast micro-bubbles and receiving echo signals of the first ultrasonic waves to generate and display a first contrast enhanced image in real time based on the echo signals of the first ultrasonic waves;

displaying a first interface having a first control article for starting collection;

in response to a click operation on the first control article for starting collection, transmitting second ultrasonic waves at a second frame rate greater than the first frame rate to the target tissue containing contrast micro-bubbles and receiving echo signals of the second ultrasonic waves;

generating and displaying a second contrast enhanced image in real time based on the echo signals of the second ultrasonic waves; and generating and displaying a super-resolution image based on the echo signals of the second ultrasonic waves; and when the current data acquisition mode is the forward acquisition mode:

in response to a second transmission instruction, transmitting third ultrasonic waves at a third frame rate greater than the first frame rate to the target tissue containing contrast micro-bubbles and receiving echo signals of the third ultrasonic waves to generate and display a third contrast enhanced image in real time based on the echo signals of the third ultrasonic waves;

displaying a second interface having a control article for super-resolution;

freezing the third contrast enhanced image in response to a click operation on the control article for super-resolution; and generating and displaying a super-resolution image based on the echo signals of the third ultrasonic waves in a period of time before freezing.

13. The contrast enhanced imaging method according to claim 12, wherein the first interface further comprises at least one of following control articles: a first control article for ending collection, a control article for timer and a control article for quantitative analysis; and the contrast enhanced imaging method further comprises:

when the current data acquisition mode is the backward acquisition mode:

in response to a click operation on the first control article for ending collection, stopping transmitting the second ultrasonic waves and/or stopping receiving the echo signals of the second ultrasonic waves, wherein the ending collection refers to stopping transmitting the second ultrasonic waves at the second frame rate greater than the first frame rate to the target tissue containing the contrast micro-bubbles and stopping receiving the echo signals of the second ultrasonic waves; and/or, in response to a click operation on the first control article for starting collection, controlling the control article for timer to start timing, and display duration for the received echo signals of the second ultrasonic waves, wherein the starting collection refers to transmitting the second ultrasonic waves at the second frame rate greater than the first frame rate to the target tissue containing the contrast micro-bubbles and receiving the echo signals of the second ultrasonic waves; and/or, in response to a click operation on the control article for quantitative analysis, performing quantitative analysis on the super-resolution image, and displaying an analysis result of the quantitative analysis.

14. The contrast enhanced imaging method according to claim 12, wherein the second interface further comprises a second control article for starting collection and a second control article for ending collection; and generating and displaying a super-resolution image based on the echo signals of the third ultrasonic waves in a period of time before freezing comprises:

displaying, in a data playback manner, an image generated by the echo signals of the third ultrasonic waves in a period of time before freezing;

in response to a click operation on the second control article for starting collection, determining a start point based on the generated image, wherein the starting collection refers to a start point of the echo signals of the third ultrasonic waves in the period of time before freezing;

in response to a click operation on the second control article for ending collection, determining an end point based on the generated image, wherein the ending collection refers to an ending point of the echo signals of the third ultrasonic waves in the period of time before freezing; and determining the echo signals of the third ultrasonic waves corresponding to a duration between the start point and the end point from the echo signals of the third ultrasonic waves in a period of time before freezing, so as to generate the super-resolution image.

15. The contrast enhanced imaging method according to claim 14, wherein the second interface further comprises at least one of the following control articles: a control article for timer and a control article for quantitative analysis; and the contrast enhanced imaging method further comprises:

when the current data acquisition mode is the backward acquisition mode:

in response to a click operation on the second control article for starting collection, controlling the control article for timer to start timing and display the duration, and in response to a click operation on the second control article for ending collection, controlling the control article for timer to end timing; and/or, in response to a click operation on the control article for quantitative analysis, performing quantitative analysis on the super-resolution image, and displaying an analysis result of the quantitative analysis.

16. The contrast enhanced imaging method according to claim 12, wherein generating and displaying a second contrast enhanced image in real time based on the echo signals of the second ultrasonic waves comprises: extracting partial frames from the echo signals of the second ultrasonic waves, and generating and displaying the second contrast enhanced image based on said partial frames; and generating and displaying a third contrast enhanced image in real time based on the echo signals of the third ultrasonic waves comprises: extracting partial frames from the echo signals of the third ultrasonic waves, and generating and displaying the third contrast enhanced image based on said partial frames.

17. The contrast enhanced imaging method according to claim 12, wherein generating and displaying a super-resolution image based on the echo signals of the second ultrasonic waves comprises: performing super-resolution data processing on the echo signals of the second ultrasonic waves to obtain said super-resolution image; and generating and displaying a super-resolution image based on the echo signals of the third ultrasonic waves in a period of time before freezing comprises: performing super-resolution data processing on the echo signals of the third ultrasonic waves in a period of time before freezing to obtain said super-resolution image.

18. The contrast enhanced imaging method according to claim 17, further comprising: displaying progress of the super-resolution data processing while performing the super-resolution data processing.

19. The contrast enhanced imaging method according to claim 12, further comprising at least one of: displaying the second contrast enhanced image and the super-resolution image on a same display interface when the current data acquisition mode is the backward acquisition mode; and, displaying the third contrast enhanced image and the super-resolution image on a same display interface when the current data acquisition mode is the forward acquisition mode.

20. An ultrasonic imaging system, comprising:

an ultrasonic probe configured to transmit ultrasonic waves and receive echo signals of the ultrasonic waves;

a transmitting and receiving control circuit configured to control the ultrasonic probe to transmit the ultrasonic waves and receive the echo signals of the ultrasonic waves;

a processor configured to perform the contrast enhanced imaging method according to any one of claim 1; and a display configured to display the super-resolution image.

21. The contrast enhanced imaging method according to claim 3, wherein the super-resolution data processing comprises:

extracting signals for contrast micro-bubbles from echo signals of ultrasonic waves to be processed;

separating the extracted signals for contrast micro-bubbles;

positioning each contrast micro-bubble;

tracking a trajectory of each contrast micro-bubble; and performing image construction based on the positioning and trajectory tracking of each contrast micro-bubble so as to obtain said super-resolution image.

* * * * *